US00PP35531P2

(12) United States Plant Patent
Tashiro

(10) Patent No.: US PP35,531 P2
(45) Date of Patent: Dec. 5, 2023

(54) ***LOBELIA* PLANT NAMED 'BALSPRINGSKL'**

(50) Latin Name: *Lobelia erinus*
Varietal Denomination: Balspringskl

(71) Applicant: Ball Horticultural Company, West Chicago, IL (US)

(72) Inventor: Rebecca M. Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/123,813

(22) Filed: Mar. 20, 2023

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./451
CPC . A01H 5/02; A01H 5/00; A01H 6/268; A01H 6/26
See application file for complete search history.

(56) References Cited

PUBLICATIONS

Ball Seed Early Springs Sky Blue Lobelia, retrieved on Jul. 17, 2023 at https://www.ballseed.com/PlantInfo/?phid=039307444000724, one page. (Year: 2023).*

Hall. Real Series: Early Springs Lobelia, Grower Talks 2015, retrieved on Jul. 17, 2023 at https://www.growertalks.com/Article/?articleid=21444, 3 pp. (Year: 2015).*

Tagawa Greenhouses 2021 Rooted Cuttings, Plugs & Prefinished Programs Ball Seed, retrieved on Jul. 18, 2023 at https://www.ballseed.com/PDF/Catalogs/Tagawa2020Catalog_20143300.pdf, cover page, 1 introductory p. 1-5, 50, 73 and back cover page. (Year: 2021).*

* cited by examiner

*Primary Examiner* — June Hwu
(74) *Attorney, Agent, or Firm* — Audrey Charles

(57) ABSTRACT

A new and distinct cultivar of *Lobelia* plant named 'Balspringskl', characterized by its medium blue-colored flowers having a white eye, medium green-colored foliage, and moderately vigorous, compact, upright-mounded, is disclosed.

1 Drawing Sheet

Latin name of genus and species of plant claimed: *Lobelia erinus*.

Variety denomination: 'Balspringskl'.

BACKGROUND OF THE INVENTION

The present invention relates to a new and distinct cultivar of *Lobelia* plant botanically known as *Lobelia erinus* and hereinafter referred to by the cultivar name 'Balspringskl'.

The new cultivar originated in a controlled breeding program in Guadalupe, California during September 2018. The objective of the breeding program was the development of heat tolerant *Lobelia* cultivars having a long flowering season with a compact, upright-mounded growth habit.

The new *Lobelia* cultivar is the result of cross-pollination. The female (seed) parent of the new cultivar is the proprietary *Lobelia erinus* breeding selection coded LOB-00313-002, not patented, characterized by its medium blue-colored flowers having a white eye, medium green-colored foliage, moderately vigorous, mounded growth habit. The male (pollen) parent of the new cultivar is the proprietary *Lobelia erinus* breeding selection coded LOB-00332-008, not patented, characterized by its light blue-colored flowers having a white throat, medium green-colored foliage, and moderately vigorous, mounded growth habit. The new cultivar was selected as a single flowering plant within the progeny of the above stated cross-pollination during April 2019 in a controlled environment in Guadalupe, California.

Asexual reproduction of the new cultivar by terminal stem cuttings since April 2019 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspringskl' as a new and distinct cultivar of *Lobelia* plant:

1. Medium blue-colored flowers having a white eye;
2. Medium green-colored foliage; and
3. Moderately vigorous, compact, upright-mounded growth habit.

Plants of the new cultivar differ from plants of the female parent primarily in having more branches per plant and more flowers per plant. Plants of the new cultivar differ from plants of the male parent primarily in having darker blue-colored flowers, more branches per plant and more flowers per plant.

Of the many commercially available *Lobelia* cultivars, the most similar in comparison to the new cultivar is Early Springs Dark Blue 'KLELE12472', U.S. Plant Pat. No. 25,289. However, in comparison, plants of the new cultivar differ from plants of 'KLELE12472' in at least the following characteristics:

1. Plants of the new cultivar have lighter blue-colored flowers than plants of 'KLELE12472'; and
2. Plants of the new cultivar have a higher slightly larger leaves than plants of 'KLELE12472'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balspringskl'. The plants were approximately 5-months old. The plants were grown in 3-gallon containers for approximately 12 weeks in an outdoor nursery in West Chicago, Illinois. Plants were given three pinches prior to transplant and one application of Daminozide at 1500 ppm after the first pinching.

DETAILED BOTANICAL DESCRIPTION

Figure 1:
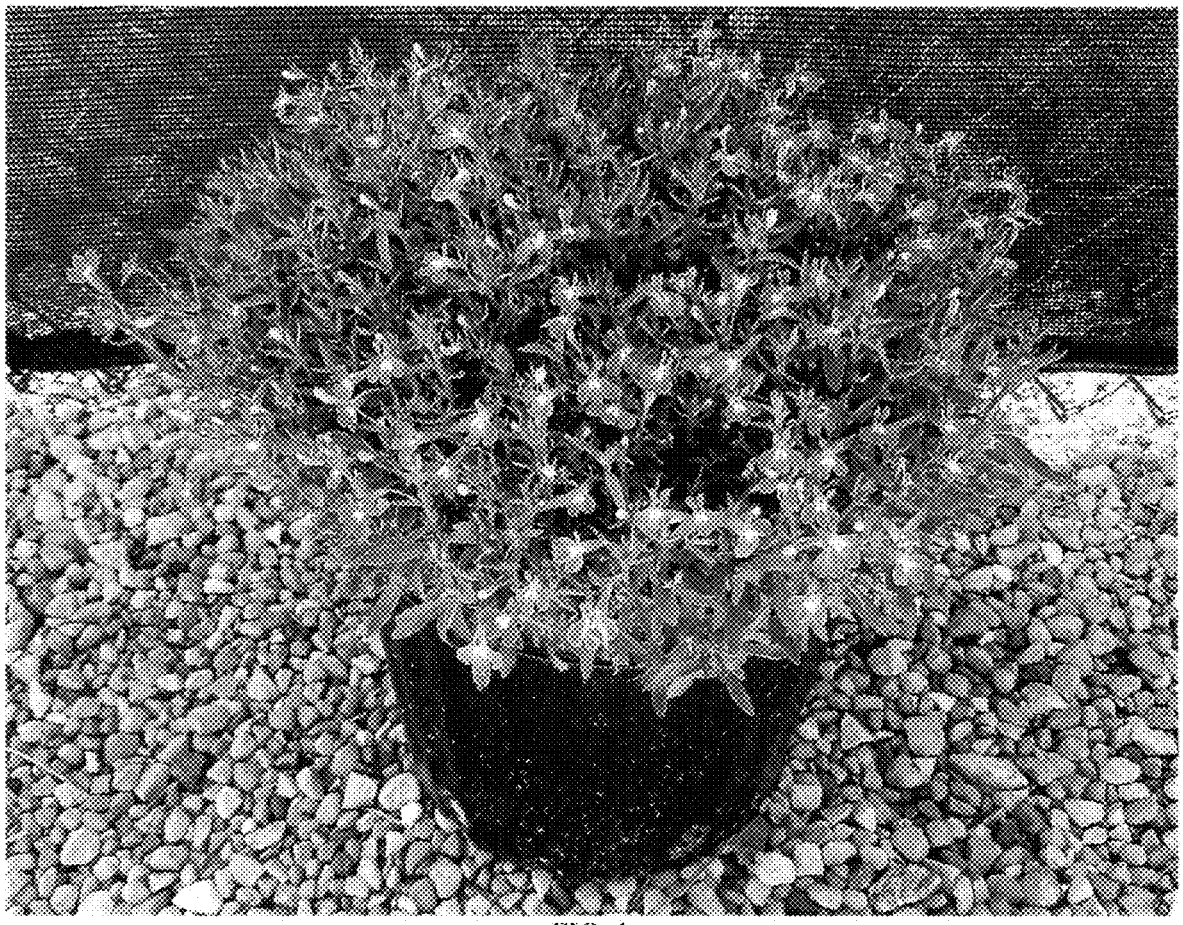
FIG. 1 illustrates a side view of the overall growth and flowering habit of 'Balspringskl'.
Figure 2:
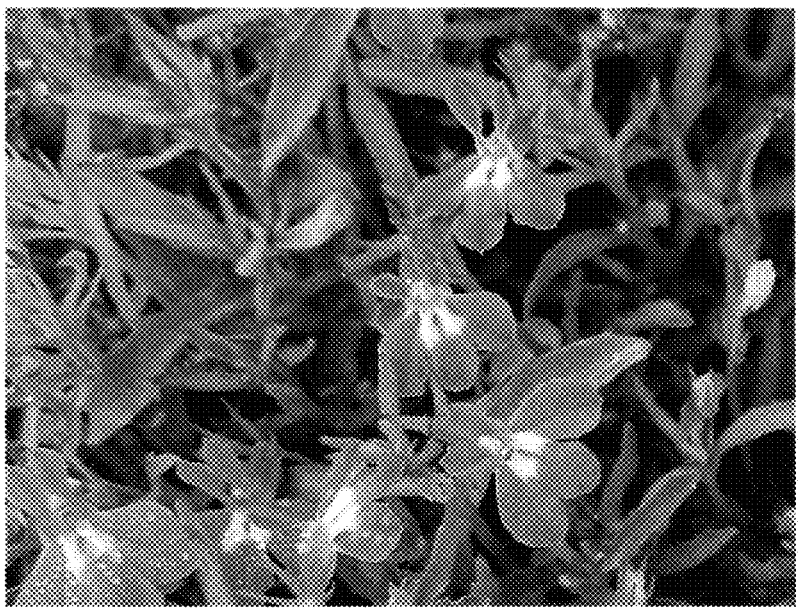
FIG. 2 illustrates a close-up view of the inflorescences of 'Balspringskl'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2022 under natural light conditions in Naperville, Illinois.

The following descriptions and measurements describe approximately 5-month-old plants produced from cuttings from stock plants and grown under conditions comparable to those used in commercial practice. The plants were grown in 3-gallon containers for approximately 12 weeks in an outdoor nursery in West Chicago, Illinois. Plants were given three pinches prior to transplant and one application of Daminozide at 1500 ppm after the first pinching. Prior to transplant plants were grown in a polycarbonate greenhouse in West Chicago, Illinois. Greenhouse temperatures were maintained at approximately 75° F. to 80° F. (24° C. to 27° C.) during the day and approximately 65° F. to 70° F. (18° C. to 21° C.) during the night. Supplemental lighting was used for first four weeks after sticking. Measurements and numerical values represent averages of typical plant.

Botanical classification: *Lobelia erinus* 'Balspringskl'.

Parentage:

*Female parent.*—Proprietary *Lobelia erinus* breeding selection coded LOB-00313-002, not patented.

*Male parent.*—Proprietary *Lobelia erinus* breeding selection coded LOB-00332-008, not patented.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fine to medium, fibrous.

*Rooting habit.*—Freely branching.

Plant description:

*Commercial crop time.*—Approximately 7 to 9 weeks from a rooted cutting to finish in a 10 cm container.

*Growth habit and general appearance.*—Moderately vigorous, compact, upright-mounded growth habit.

*Size.*—Height from soil level to top of plant plane: Approximately 20.0 cm. Width: Approximately 41.0 cm.

*Branching habit.*—Freely branching, pinching enhances lateral branching. Attitude: Upright to semi-right. Quantity of branches per plant: Approximately 8 main branches with approximately 12 lateral branches per main branch.

*Lateral branch.*—Shape: Square in cross section. Strength: Strong, flexible. Length: Approximately 18.5 cm. Diameter: Approximately 2.0 mm to 3.0 mm. Length of central internode: Approximately 1.5 cm. Texture: Moderately pubescent. Color of young stems: 144A. Color of mature stems: 146B.

Foliage description:

*General Description.*—Quantity of leaves per branch: Approximately 8. Fragrance: None detected. Form: Simple. Arrangement: Alternate.

*Leaves.*—Aspect: Acute angle to stem. Shape: Narrowly elliptic. Margin: Shallowly serrate. Apex: Acute. Base: Sessile. Venation pattern: Pinnate. Length of mature leaf: Approximately 3.0 cm. Width of mature leaf: Approximately 7.0 mm. Texture of upper surface: Moderately pubescent. Texture of lower surface: Densely pubescent. Color of upper surface of young and mature foliage: 137A with venation of 137B. Color of lower surface of young and mature foliage: 138B with venation of 138A.

Flowering description:

*Flowering habit.*—'Balspringskl' is freely flowering under outdoor conditions with substantially continuous blooming from early spring through summer and year-round in a greenhouse environment.

Inflorescence description:

*General description.*—Type: Loose raceme. Quantity per plant: Approximately 115. Fragrance: None detected. Length or height of inflorescence: Approximately 3.5 cm to 5.5 cm. Width of inflorescence: Approximately 2.5 cm to 3.5 cm. Quantity of fully-open flowers per inflorescence: Approximately 1 to 3.

Flower description:

*Type.*—Single, zygomorphic, bilabiate.

*Bud just before opening.*—Shape: Oblanceolate. Length: Approximately 1.3 cm. Diameter at distal end: Approximately 4.0 mm. Diameter at proximal end: Approximately 2.0 mm. Texture: Densely pubescent. Color: 154D with stripes of 95C.

*Corolla.*—Shape: Bilabiate having an upper lip of two narrow lobes and a lower lip of three lobes. Lobes are fused at the base forming a tube that is split between the two upper lobes. Aspect: Facing upward and outward. Width: Approximately 1.6 cm. Length: Approximately 1.8 cm. Depth: Approximately 2.0 cm.

*Upper lobes.*—Shape: Oblanceolate. Margin: Entire, ciliate. Apex: Mucronate. Length from throat: Approximately 7.0 mm. Width: Approximately 3.0 mm. Texture of upper surface: Sparsely pubescent near base. Texture of lower surface: Glabrous. Color of upper surface when first open: N95C. Color of lower surface when first open: NN155D with an irregular overlay of 94C. Color of upper surface when fully open: 95C. Color of lower surface when fully open: NN155D with an irregular overlay of 95D.

*Lower lobes.*—Shape: Obovate. Arrangement: Touching. Margin: Entire. Apex: Mucronate to rounded. Length from throat: Approximately 1.1 cm. Width: Approximately 5.0 mm, middle lobe broad. Texture of upper surface: Sparsely pubescent near base. Texture of lower surface: Sparsely pubescent. Color of upper surface when first open: N95D with NN155D at base in rounded shape. Color of lower surface when first open: NN155D with an irregular overlay of 94C. Color of upper surface when fully open: 95C with NN155D at base in rounded shape. Color of lower surface when fully open: NN155D with an irregular overlay of 95D.

*Corolla tube.*—Length: Approximately 9.0 mm. Width at opening: Approximately 4.0 mm. Width at base: 2.0 mm. Texture of inner surface: Glabrous with sparse pubescence at throat opening. Texture of outer surface: Sparsely pubescent. Color of inner surface: NN155D with two nectary tracks of 144A. Color of outer surface: 95C to 95D with NN155D.

*Calyx.*—Shape: Star. Length: Approximately 9.0 mm. Diameter: Approximately 1.1 cm.

*Sepals.*—Quantity per flower: 5. Shape: Lanceolate. Margin: Entire, ciliate. Apex: Acute. Base: Fused into cup-like structure. Length of free portion: Approximately 7.0 mm. Width: Approximately 1.0 mm. Texture of inner surface: Glabrous. Texture of outer surface: Moderately pubescent. Color of inner and outer surfaces: 146A with N186A at tip and on margins.

*Pedicel.*—Strength: Strong, flexible. Aspect: At an acute angle. Length: Approximately 2.2 cm. Diameter: Approximately 1.0 mm. Texture: Moderately pubescent. Color: 146B.

*Reproductive organs.*—Androecium: Stamen quantity: 5 per flower, upper half of filaments connate. Stamen length: Approximately 9.0 mm. Filament color: 95C to 95D with NN155D. Anther shape: Oblong. Anther length: Approximately 2.0 mm. Anther color: 155D transitioning to 199A with 199B. Pollen amount: None observed. Gynoecium: Pistil quantity: 1 per flower. Pistil length: Approximately 1.1 cm. Stigma shape: Bilobate. Stigma length: Approximately 1.0 mm. Stigma color: N88A. Style length: Approximately 8.0 mm. Style color: 145A. Ovary length: Approximately 2.0 mm. Ovary color: 146A.

Seed and fruit production: Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balspringskl', substantially as herein illustrated and described.

* * * * *